United States Patent [19]

Jevne et al.

[11] Patent Number: 4,650,614
[45] Date of Patent: Mar. 17, 1987

[54] REFINING OF REACTION GRADE 2-ACRYLAMIDO-2-METHYLPROPANE SULFONIC ACID

[75] Inventors: Allan H. Jevne, Anoka; Patrick T. Cahalan, Champlin; Arthur J. Coury, St. Paul, all of Minn.

[73] Assignee: Medtronic, Inc., Minneapolis, Minn.

[21] Appl. No.: 402,254

[22] Filed: Jul. 27, 1982

Related U.S. Application Data

[63] Continuation-in-part of Ser. No. 123,356, Feb. 21, 1980, abandoned.

[51] Int. Cl.$^4$ .............................................. C07C 143/02
[52] U.S. Cl. ................................................ 260/513 N
[58] Field of Search ..................................... 260/513 N

[56] References Cited

PUBLICATIONS

"Process for the Production of Refined AMPS", 12/76.
Weissberger, "Separation & Purification", Part I, 2nd ed. (1956), pp. 548–549, 742–744.
Lubrizol Grp Brochure.

*Primary Examiner*—Alan Siegel
*Attorney, Agent, or Firm*—Vidas & Arrett

[57] ABSTRACT

Reaction grade 2-acrylamido-2-methylpropane sulfonic acid is refined by mildly heating a slurry-like suspension formed of the acid and a liquid monohydric alcohol, recovering the acid from the alcohol and subsequently drying it.

31 Claims, No Drawings

REFINING OF REACTION GRADE 2-ACRYLAMIDO-2-METHYLPROPANE SULFONIC ACID

This is a continuation-in-part application of copending patent application Ser. No. 123,356, filed Feb. 21, 1980, entitled "REFINING OF 2-ACRYLAMIDO-2-METHYLPROPANE SULFONIC ACID", now abandoned. This continuation-in-part application is assigned to the same assignee as is the parent application i.e., Medtronic, Inc.

BACKGROUND OF THE INVENTION 2-acrylamido-2-methylpropane sulfonic acid is a white crystalline solid having a melting point of about 185° C., a molecular weight of 207 and a Neutralization Equivalent of 207. It is commercially available from Lubrizol Corporation, Wickliffe, Ohio, and is sold by that corporation under the trademark AMPS. The acid is a monomer which is generally polymerized for a variety of uses. One such use is in medical electrodes particularly adapted to tape-like configurations for use in sensing and stimulation applications in which the electrode is applied to the skin. In such a use, one electrode component comprises 2-acrylamido-2-methylpropane sulfonic acid in a polymerized form. The polymer, in the solid solution or gel form, possesses electrically conductive properties, flexible properties and adhesive properties, particularly lending itself to skin contact and adhesion.

As presently available in a "reaction" grade from Lubrizol, the acid contains trace amounts of alkyl sulfonic acids which are believed to act as chain transfer agents, reducing ultimate molecular weight achieved during polymerization.

Lubrizol Corporation has on occasion made the acid available in a "refined" grade. In preparing the "refined" grade according to the Lubrizol procedure, the acid is subjected to a refining method consisting of: dissolving the acid in methylalcohol at elevated temperatures on the order of 175°–180° F., filtering the solution to remove any undissolved matter and recrystalizing the acid from the solution. Polymers from the "refined" grade exhibit higher molecular weights and improved properties.

It is a purpose of this invention to provide an improved method of refining reaction grade 2-acrylamido-2-methylpropane sulfonic acid which has not previously undergone the dissolution and recrystallization steps used in the Lubrizol refining procedure referred to above.

BRIEF SUMMARY OF THE INVENTION

In accordance with the improved method of the invention, solid reaction grade 2-acrylamido-2-methylpropane sulfonic acid, which has not previously undergone the dissolution and recrystallization steps used in the Lubrizol refining procedure is mixed with a liquid monohydric alcohol such as methyl alcohol, ethyl alcohol or isopropyl alcohol to form a solid-in-liquid suspension, herein termed a "slurry". The amount of acid used relative to the alcohol is not critical. The slurry is agitated and mildly heated i.e., to a temperature below that at which any significant dissolution of the acid in the alcohol or reaction between the acid and the alcohol can occur. In most instances, the upper temperature limit will be set by the boiling point of the alcohol involved. Preferably, the heating temperature will be substantially below the boiling point of the alcohol. The system in which heating takes place may be closed or open with a dry atmosphere. Following heating, the acid is separated from the alcohol and dried.

In this invention, dissolution and reprecipitation or recrystallization of the acid is substantially avoided; only washing occurs. Additionally, the method of the invention provides higher yields than the prior art method (i.e., 85–90% vs. 60–75%) due to the fact that reaction grade AMPS is used which has not previously undergone the dissolution and recrystallization steps of the above-identified and described Lubrizol refining process. Furthermore, the higher yields are obtained at a lower cost due to the lower volumes of alcohol and lower energy consumption required by this improved method. Additionally, the method is safer since no reactor pressure is involved. Also, the method of the invention is less complicated and provides more consistent and uniform results.

DETAILED DESCRIPTION OF THE INVENTION

Generally, this invention provides a method for purifying reaction grade 2-acrylamido-2-methylpropane sulfonic acid, as obtained commercially, by a short duration, mild heating of the acid in a slurry with a volatile liquid monohydric alcohol followed by acid recovery via decantation or other form of separation and subsequent drying of the wet solid acid. The acid is "reaction grade", i.e., it has not previously undergone dissolution or recrystallization by refining. In the method of the invention, only washing of the acid occurs, i.e., the acid is not substantially dissolved.

A preferred embodiment of the method involves the following steps:
(a) Agitation of a 30% by weight mixture of the reaction grade acid, i.e., acid which has not previously undergone the dissolution and recrystallization steps used in the Lubrizol refining procedure, in commercially available anhydrous methyl alcohol for two hours at 40° C.;
(b) Separation of the acid by centrifugation;
(c) Drying of the wet acid in a rotary vacuum dryer at 50° C. for two hours.

Alternate preferred embodiments of the above method include one or more of the following:
(a) Substitution of absolute ethyl alcohol or anhydrous isopropyl alcohol for the methyl alcohol;
(b) Utilization of a slurry that contains 25–35% by weight acid;
(c) Agitating the suspension for one-half to 24 hours at 25°–60° C.;
(d) Separation of the acid from the alcohol by means of gravity filtration, pressure filtration, vacuum filtration or centrifugation;
(e) Drying at 25°–70° C. either under vacuum or at ambient pressure to substantially remove the alcohol, the drying time preferably being minimized as much as possible.

It can be seen from the above that, basically, the method of the invention involves forming a suspension of the acid in a liquid monohydric alcohol without dissolution and recrystallization, separating the acid from the alcohol and drying the separated acid.

EXAMPLE

To a 5-liter, 3-necked round bottom flask equipped with magnetic stirrer, thermometer, condenser and drying tube, 1071 grams of reaction grade 2-acrylamido-2-methylpropane sulfonic acid and 2500 grams of anhydrous methyl alcohol (analytic reagent grade) are added. The acid has not previously undergone the dissolution and recrystallization steps used in the Lubrizol refining procedure.

The resultant slurry is agitated and heated to 40° C. The 40° C. pot temperature is maintained for 2 hours. After that time, the heating mantle is withdrawn and the slurry is cooled with an external water bath for 1½ hours. The slurry at 20° C. is then vacuum filtered through No. 4 Whatman paper (15 cm) in a Buchner funnel. Filtration time is approximately ½ hour (rapid filtration). The isolated solid, containing 20% methyl alcohol, is transferred to a 50° C. vacuum oven and dried of methyl alcohol in 3 hours at approximately 1 mm Hg pressure. The yield of refined acid will be about 82% based on starting acid weight. Such a refined acid was solution polymerized by means of a Redox catalyst system to yield a product with acceptable properties for use in skin electrodes.

EXAMPLE

The optimum equipment for purifying a 500-lb batch of the acid according to the method of the invention comprises a 500-gallon glass-lined steel, agitated, closed reactor equipped with a cooling jacket; a 316-type stainless steel perforated bowl centrifuge for solids isolation, and a rotary vacuum dryer. All equipment must be clean.

A 500-lb batch is refined as follows:

500 lbs reaction grade 2-acrylamido-2-methylpropane sulfonic acid which has not previously undergone the dissolution and recrystallization steps used in the above-described Lubrizol refining procedure and 1167 lbs anhydrous methyl alcohol are transferred into a dry, $N_2$ flushed reactor. The reactor ventline is equipped with a desiccant to prevent moisture uptake from the outside atmosphere. The reactor contents are agitated to form the slurry and heated by an external heat exchanger to 40° C. The 40° C. pot temperature is maintained for 2 hours. After that time cooling is initiated and the agitated slurry is held at 20° C. or less for 1½ hours. Centrifugation of the slurry can be started after that time. Immediately upon completion of centrifugation, the isolated wet acid is dried at 50°-70° C. in a rotary vacuum dryer.

Throughout the refining procedure, effort is made to exclude contamination by atmospheric moisture to prevent yield loss due to increased acid solubility. In this connection, it is also preferred that anhydrous methyl alcohol, anhydrous isopropyl alcohol or absolute ethyl alcohol be used in forming the slurry. All of these are commercially available. The use of these kinds of liquid monohydric alcohols minimize the yield loss by avoiding the condition in which the solubility of the acid in such alcohols is enhanced by the presence of water. As can be seen from the solubility table included hereinbelow, the acid monomer is relatively soluble in water as compared to the alcohols.

| SOLUBILITY TABLE | | |
|---|---|---|
| Solvent | Solubility g/100 g solvent | Temp. °C. |
| Water | 150 | 25 |
| Methanol | 8.7 | 30 |
| Ethanol | 10 | 78* |
| Isopropanol | 6 | 82* |

(*boiling point of solvent)

As indicated above, it is preferred that the slurry be mildly heated to a relatively low temperature of about 40°-60° C. during refining. The exact temperature is not critical and cannot be exactly specified since it is in large part dependent upon the particular alcohol utilized. In most instances, the upper temperature limit will be the boiling point of the particular alcohol being utilized. If the heating temperatures are maintained substantially below such values, as is preferred, no significant dissolution of the acid into the alcohol will occur. This can be seen by referring to the Solubility Table above. The Table also demonstrates that, in the case of methanol, it is preferred that the temperature be substantially below the boiling point. Consequently, yield loss will be minimized. Additionally, at higher slurry temperatures, alcoholysis of the acid occurs and yield loss will result.

If centrifuging is selected for separating the refined acid from the alcohol, centrifugation may be accomplished batch-wise. The batch-wise technique developed by Lubrizol Corporation is satisfactory for this purpose. One such arrangement utilizes a 24-inch basket centrifuge. 400 lbs of slurry are fed to the centrifuge spinning at 500 rpm. Filling flow rate is adjusted so that it takes approximately 10 minutes for the basket to fill. After a 5-minute spin at 1500 rpm, the speed is reduced to 800 rpm and the resultant acid cake is rinsed for 2 minutes with methyl alcohol. The cake is spun dry at 1500 rpm for 10-15 minutes. The wet cake, which typically contains 10-15% methyl alcohol, is manually removed and charged to a dryer.

A jacketed Stokes rotary vacuum dryer may be utilized for drying. A 2-stage Fuller rotary vane vacuum pump may be used. A direct contact condenser, using −20° C. methyl alcohol as the cooling liquid, is preferably placed on the inlet of the vacuum source. In addition to condensing methyl alcohol, the spray of circulating methyl alcohol also scrubs out the acid dust. Typically, a 480 lb wet cake may be dried in 2.5 hours in such a set up. A batch may be considered dry when the dryer absolute pressure drops to 10 mm Hg. The contents of the dryer may then be packaged.

Having described the invention by reference to preferred embodiments for illustration, exclusive property rights therein are defined by the following claims.

We claim:

1. A method of refining solid reaction grade 2-acrylamido-2-methylpropane sulfonic acid which has not previously undergone the dissolution and recrystallization steps used in the Lubrizol refining procedure, consisting of the steps:
   mixing a quantity of the solid acid with a quantity of a liquid monohydric alcohol without significant dissolution of the acid;
   agitating the mixture;
   separating the solid acid from the alcohol; and drying the acid to substantially remove any remaining alcohol.

2. The method of claim 1 wherein the mixture contains about 25–35% by weight of the acid.

3. The method of either of the foregoing claims 1 or 2 wherein the mixture is heated for a time, the heating temperature being below that which would cause any significant dissolution of the acid in the alcohol.

4. The method of either of the foregoing claims 1 or 2 wherein the mixture is heated to a temperature below the boiling point of the alcohol.

5. The method of either of the foregoing claims 1 or 2 wherein the mixture is heated to a temperature between about 25° C. to about 60° C.

6. The method of claim 5 wherein the heating period is between about ½ hour and about 24 hours.

7. The method of claim 1 wherein separation of the acid from the alcohol is effected by filtration.

8. The method of claim 1 wherein separation of the acid from the alcohol is effected by centrifugation.

9. The method of claim 1 wherein drying of the refined acid is effected by vacuum drying.

10. The method of claim 1 wherein drying of the refined acid is effected by heating under a vacuum or at ambient pressure.

11. The method of claim 10 wherein the heating temperature is between about 25° C. and 70° C.

12. The method of claim 1 wherein the alcohol is selected from the group consisting of methyl alcohol, ethyl alcohol, isopropyl alcohol and mixtures thereof.

13. The method of claim 12 wherein the alcohol is anhydrous methyl alcohol.

14. The method of claim 12 wherein the alcohol is anhydrous isopropyl alcohol.

15. The method of claim 12 wherein the alcohol is absolute ethyl alcohol.

16. The method of claim 3 wherein the mixture is cooled before separation of the acid from the alcohol is effected.

17. The method of claim 11 wherein the drying is effected for a period of between about 2–3 hours.

18. The method of claim 9 wherein drying is effected in a rotary vacuum dryer.

19. A method of refining solid reaction grade 2-acrylamido-2-methylpropane sulfonic acid which has not previously undergone the dissolution and recrystallization steps used in the Lubrizol refining procedure, consisting of the steps:
    mixing the solid acid in an alcohol selected from the group consisting of methyl alcohol, ethyl alcohol, isopropyl alcohol, and mixtures thereof without substantial dissolution of the acid;
    agitating the mixture for between about ½ to 2 hours at a temperature of between about 25°–60° C.;
    separating the solid acid from the alcohol; and
    drying the acid.

20. The method of claim 19 wherein the mixture contains about 25–35% by weight acid.

21. The method of claim 19 wherein separation is by filtering or centrifugation.

22. The method of claim 19 wherein drying is effected under vacuum at 50° C. for between about 2–3 hours.

23. The method of claim 22 wherein the vacuum level is about 1 mm Hg pressure.

24. The method of claim 19 wherein the methyl alcohol is anhydrous.

25. The method of claim 19 wherein the mixture is cooled to about 20° C. or less before separation is effected.

26. The method of claim 25 wherein the mixture is held at the cooling temperature for about 1½ hours prior to separation of the acid from the alcohol.

27. The method of claim 19 wherein the percent by weight of the acid is 30%.

28. The method of claim 19 wherein the mixing time is about 2 hours.

29. The method of claim 19 wherein the mixing temperature is about 40° C.

30. The method of claim 19 wherein the isopropyl alcohol is anhydrous.

31. The method of claim 19 wherein the ethyl alcohol is absolute.

* * * * *